United States Patent [19]

Masi

[11] Patent Number: 5,393,392
[45] Date of Patent: Feb. 28, 1995

[54] POLAROGRAPHIC PPB OXYGEN GAS SENSOR

[75] Inventor: Robert J. Masi, Littleton, Mass.

[73] Assignee: Delta F Corporation, Woburn, Mass.

[21] Appl. No.: 232,747

[22] Filed: Apr. 25, 1994

[51] Int. Cl.$^6$ ............................................. G01N 27/26
[52] U.S. Cl. ................................ 204/153.16; 204/409;
204/432; 204/258; 204/265; 204/266; 204/277;
204/278; 204/412
[58] Field of Search ............... 204/412, 424, 432, 409,
204/431, 258, 265, 266, 277, 278, 284, 290 R,
291, 292, 153.16

[56] References Cited

U.S. PATENT DOCUMENTS 4,960,497 10/1990 Gallagher ..................... 204/153.16
5,256,273 10/1993 Gallagher et al. ................ 204/424

*Primary Examiner*—John Niebling
*Assistant Examiner*—Bruce F. Bell
*Attorney, Agent, or Firm*—Samuels, Gauthier & Stevens

[57] ABSTRACT

A polarographic electrochemical cell for the measurement of oxygen in ppb. The cathode in the system is a non-depleting carbon polytetrafluoroethylene electrode catalytically specific for oxygen reduction. The anode is a composite nickel matrix. The reaction at the anode is an electrochemical oxidation reaction but there are no soluble byproducts that contaminate the electrode. The reaction at the anode is a simple oxidation, state-of-change of the nickel in the nickel composite matrix.

32 Claims, 1 Drawing Sheet

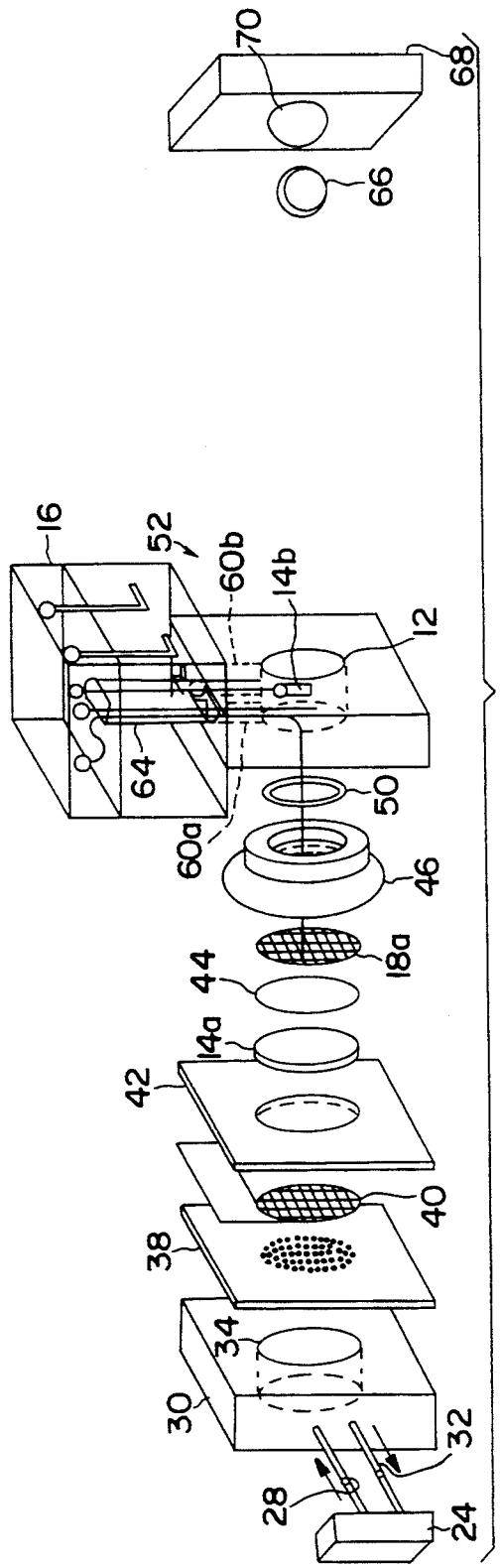
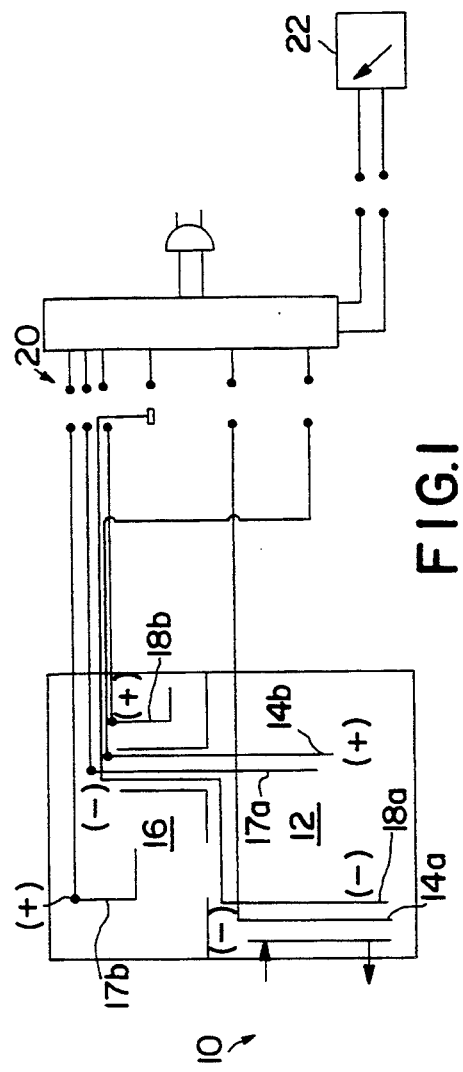
FIG.1
FIG.2

POLAROGRAPHIC PPB OXYGEN GAS SENSOR

BACKGROUND AND BRIEF SUMMARY OF THE INVENTION

An electrochemical cell, in its simplest terms, consists of an anode (the oxidizing electrode), a cathode (the reducing electrode) and an electrolyte. In order for the electrochemical cell to function, the electrolyte must be compatible with the mechanisms of oxidation and reduction at the electrodes. As well, it must provide a conductive path for the transport of ionic species between the electrodes.

The electrochemical cell concept is broadly applied in industrial and scientific operations. Electrolytic cells are used in electroplating, water purification, and the production of high purity gases and metals, while electrochemical cells, such as batteries and fuel cells provide a convenient means of energy storage and generation.

Also, due to their very high level of sensitivity, electrochemical cells are used for measurement in a variety of analytical procedures and many laboratory and process control instruments depend on the electrochemical cell as the sensing element for their function.

U.S. Pat. No. 4,960,497 discloses a system wherein an electrolytic cell measures oxygen in the ppb range. In this system, the dissolved oxygen in the electrolyte is removed to allow for an accurate reading of the oxygen concentration in a gas sample. However, in this system, when measuring in the 0–100 ppb range, it was found that in some instances the signal-to-noise ratio was not high enough to provide a consistently accurate reading.

There are other electrochemical systems currently available which measure oxygen in the 0–100 ppb range. These sensors are known as galvanic or battery type systems that use lead or cadmium as the anode. In these systems, as oxygen is measured by the sensor, the lead or cadmium anode is consumed. There are several inherent drawbacks in the use of these consumable anodes. One drawback is that the critical cathodic potential is determined directly by anodic potential, since these systems are galvanic (no applied potential). The anodic potentials of lead and cadmium drift as the electrodes are consumed thus affecting the stability of the critical cathodic potential. Drift in the cathodic potential will result in calibration drift. A second drawback to using lead or cadmium is that as the anodes are consumed they produce byproducts that are soluble in the electrolyte solution. These byproducts are free to migrate to the cathode and contaminate the electrode surface causing further calibration drift.

U.S. Pat. No. 5,256,273 disclosed a stable electrochemical system and a method for measuring an analyte, i.e. oxygen in the 0–100 ppb range. The system functioned as a hydrogen-oxygen alkaline fuel cell configured to generate current which was linear to the rate at which the analyte was either reduced at a cathode, i.e. oxygen or oxidized at the anode, i.e. hydrogen. That system provided consistently accurate readings in the 0–100 ppb range for oxygen. The system exhibited very little calibration drift because the anode was not consumed during measurement and therefore maintained a stable potential. A second reason for the excellent calibration stability can be attributed to the fact that there were no soluble byproducts of the hydrogen anode reaction. However, the presence of a hydrogen source with the system in some instances raised safety considerations.

The present invention embodies a system and a process for measuring oxygen, particularly in the 0–100 ppb range. The system is a polarographic system using an anode which is specifically designed for long-term potential stability, high electrochemical reversibility and chemical inertness. For oxygen analysis, the cathode used is the same as the prior art system described in U.S. Pat. No. 5,256,273; namely, the cathode is a non-depleting carbon Teflon electrode catalytically specific for oxygen reduction. At the anode an electrochemical oxidation reaction occurs but there are no soluble byproducts that contaminate the electrolyte. The reaction at the anode is a simple oxidation state change of nickel in a nickel composite matrix. As current flows through the sensor during oxygen measurement, the ratio of $Ni+2/Ni+3$ changes in the composite matrix, however, the anodic potential remains very stable. The composite matrix is designed for stability in KOH which is the preferred electrolyte. This anode reaction is highly reversible meaning that the anodic potential will not change as a function of the current produced by oxygen measurement. By operating this system polarographically, the cathodic potential can be adjusted to any level which is deemed optimal for maximum signal-to-noise ratio. The amount of nickel actually oxidized during usage is so minimal that in essence, the anode is nondepleting.

In the preferred embodiment of the invention, a nickel electrode specifically having the composition 50% $Ni(OH)_2$ and 50% NiOOH is used. An anode used in the system of the invention having a surface area of 8 $in^2$ and a weight of six grams would be expected to perform satisfactorily when measuring in the sub 100 ppb range of a period approaching 30 years. If desired, the nickel anode can be restored in situ back to its original $Ni+2/Ni+3$ ratio.

In the preferred embodiment, the invention comprises an polarographic electrochemical cell. A gaseous stream containing the oxygen to be measured contacts a cathode catalytically optimized for oxygen. The oxygen is reduced forming hydroxyl ions. The hydroxyl ions react with the metal anode. The metal anode is oxidized. Collectively these reactions generate a current which is proportional to the rate at which oxygen is reduced at the cathode. The current measured corresponds exactly to the changing concentration of oxygen in the gaseous stream.

Although the preferred embodiment uses a nickel electrode with a composition of 50% $Ni(OH)_2$ and 50% NiOOH, other metal anodes believed suitable for purposes of the invention include $MnO_2/MnOOH$, $Ag_2O/Ag_2O_2$, and $Hg/HgO$.

One advantage of this invention is that the system is a clean system, the byproduct of the anodic reaction is simply a change in the oxidation state of the metal composite anode. With a lead anode or a cadmium anode there are discrete chemical reaction byproducts which build up in the sensor cell and act as inhibitors to the electrochemical reactions.

Distinct advantages over the previous ppb oxygen sensor system disclosed in U.S. Pat. No. 4,960,497 include higher oxygen sensitivity, lower background offset, less offset drift, improved linear response, improved speed of response and reduced temperature sensitivity.

BRIEF DESCRIPTION OF THE DRAWINGS

FIG. 1 is a functional block diagram of an embodiment of the invention; and

FIG. 2 is an exploded perspective view of an embodiment of the invention.

DESCRIPTION OF THE PREFERRED EMBODIMENT(S)

Referring to FIG. 1, a block diagram of an electrochemical system 10, of the preferred embodiment of the invention is shown. The system 10 includes an electrochemical cell cavity 12 having two sensing electrodes 14a and 14b and two additional electrodes 18a and 17a disposed therein. Electrolyte in a reservoir 16 is in fluid flow communication with the electrolyte in the cell cavity 12. The reservoir 16 includes an electrode 17b and an electrode 18b. The polarographic potential for the sensing electrodes 14a and 14b is provided by a DC circuit and power conditioner 20. The electrolyte in cell cavity 12 with the electrodes 14a and 14b completes the electrolytic circuit. The power conditioner 20 applies a constant potential across electrodes 18a and 18b by a separate DC circuit (not shown). The electrolyte common to the cell cavity 12 and reservoir 16 completes the electrolytic circuit. The power conditioner 20 also provides a constant current across electrodes 17a and 17b via a third separate DC circuit (not shown). The electrolyte common to the cell cavity 12 and reservoir 16 completes the electrolytic circuit. Although also not shown, the power conditioner will include the appropriate resistors, amplifiers, etc. in order to control specifically the circuit condition required by each of the three independent sets of electrodes. A meter 22 communicates with electrodes 14a and 14b via the power conditioner 20 to provide a direct reading corresponding to the electro-reduction of the oxygen to be analyzed.

Referring to FIG. 2, the cell cavity 12 and reservoir 16 are shown in greater detail. A gaseous stream containing the oxygen to be measured flows from a source 24 through an inlet 28 and into an inlet plate 30. The inlet plate 30 includes a cavity-like recess 34 through which the gaseous stream flows. An apertured diffuser plate 38 meters the diffusion of oxygen in the sample stream to the electrode 14a. A current collector 40 is sandwiched between the diffuser plate 38 and an electrode retainer plate 42 having an aperture therein. The electrode 14a is received in the aperture. A non-conductive permeable separator 44 is interposed between the electrode 14a and a platinum screen electrode 18a. An electrolyte plate 46 having flow passages therein abuts the electrode 18a on one side and on the other side receives an O-ring 50.

The electrode 14b is rigidly suspended in the cavity 12.

Conduits 60a and 60b are formed in the cell cavity housing 12 and are received in the bottom of the reservoir 16. The wires for the electrodes 14a, 17a and 18a pass through the conduit 60a. A sleeve 64 in the reservoir 16 is placed over the conduit 60a to isolate the electrodes 17a and 18a from electrodes 17b and 18b. The electrodes 17b and 18b are secured in any suitable manner within the reservoir 16. The electrolyte in the cell cavity 12 and the reservoir 16 are in fluid flow communication with one another only via the conduit 60b.

On the other side of the housing 52 are an O-ring 66 and a plate 68 with a recess 70 which sealingly engages the O-ring 66.

The electrode 14a (which functions as a cathode) is generally any semi-permeable electrode catalytically specific to oxygen. A non-specific cathode may be used as long as the rate of oxygen reduction at the cathode is proportional to the oxygen diffusion rate through the diffuser plate 38. The electrode 14b is a highly reversible electrode such as a nickel hydroxide/nickel oxyhydroxide composite.

The electrode 17a is preferably a metal such as nickel and the corresponding electrode 17b is platinum.

The electrode 18a, specifically a barrier electrode, is preferably a platinum wire mesh. The corresponding electrode 18b is preferably a platinum rod.

OPERATION OF THE INVENTION

In the operation of the invention, an aqueous electrolyte (such as a solution of 1M potassium hydroxide) is introduced into the reservoir 16 and cell cavity 12. A first electrolytic path is established between electrodes 14a and 14b in the cell cavity 12. Based on the electrode potential of the electrode 14b, an external potential is applied to maintain the cathodic potential at a desired level, e.g. for the preferred embodiment 1.3 VDC.

A second electrolytic path is established between the electrodes 17a and 17b and a third electrolytic path is established between the electrodes 18a and 18b. The second and third electrolytic paths use the electrolyte common to the cell cavity 12 and the reservoir 16. The three pairs of electrodes 14a–14b, 17a–17b, and 18a–18b are connected to the power conditioner 20 through appropriate connectors (not shown). The power conditioner 20 includes an appropriate circuit which provides a small continuous current between electrodes 17a and 17b. The power conditioner 20 includes an appropriate measurement circuit to sense the current produced electrochemically by electrodes 14a and 14b. The power conditioner 20 provides a 1.5 VDC potential which is placed across electrodes 18a and 18b.

A gaseous sample stream 24 containing some finite concentration of oxygen flows through inlet plate 30. A flow rate of between 0.5 to 3 scfh is preferred. The gas may be at a temperature of between 32°–120° F. and at a pressure of about 0–1 psi gauge.

Oxygen in the sample stream diffuses through the diffuser plate 38 and is electrochemically reduced at electrode 14a. This electrode 14a, which functions as a cathode, is preferably a metal catalyzed carbon-Teflon electrode. The electrode 14b is a nickel composite and functions as an anode.

In this embodiment, oxygen is electrochemically reduced at electrode 14a producing hydroxyl ions OH−. The hydroxyl ions migrate across the cell cavity 12 to electrode 14b where they complete the ionic circuit and change the oxidation state of the nickel from +2 to +3.

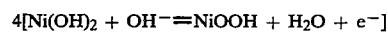

$$4[Ni(OH)_2 + OH^- = NiOOH + H_2O + e^-]$$

The sensing device 10 produces current in exact proportion with the rate at which oxygen in the sample gas diffuses to electrode 14a. The current produced (i.e. the oxygen diffusion rate) is exactly linear with the changing oxygen concentration when the sensor is operated in the current limiting region. The current produced by the sensor when oxygen is present in the gaseous sample 24 is measured by the power conditioner 20 and displayed by the meter 22. For example, with a 7 ppm oxygen concentration in the gas sample 24, the diffusion rate of oxygen to electrode 14a is approximately 4.7 E-3 cc/hr and produces a current of 21 micro-amps in the cell. When the oxygen concentration in the gas sample 24 is reduced to 70 ppb the cell current is linearly reduced to 210 nano-amps, thus providing an ideally linear response to changing oxygen concentration.

Electrodes 17a and 17b perform a separate function which is integral to the operation of the sensing device 10 in the ppb range. They provide a mechanism to remove and/or entrap trace ionic impurities in the electrolytic solution. The introduction of such trace impurities into the electrolyte may come from one or all of three possible sources: they are present in the original electrolytic solution; secondly, they are introduced into the electrolytic solution as a result of separate chemical reactions between the materials of construction of the sensor (including the electrodes) and the electrolyte; and lastly, they enter as contaminants, e.g. acid gases, from the gaseous sample streams.

The elimination of, or protection against, these trace ionic impurities is important in the monitoring of trace (<100 ppb) oxygen streams. With cell current continually reducing, as when measuring lower and lower oxygen concentrations, trace ionic impurities become more problematic for stable sensing. These impurities may be strongly adsorbed at the active sites and thus lower the effective surface area for oxygen reduction. Trace ionic impurities also influence the adsorption of reactants or intermediates which may alter the electrochemical sensitivity to oxygen. The presence of electrodes 17a and 17b at an applied potential and fixed current has a scavenging effect on trace ionic impurities in solution, thus protecting the oxygen sensing electrodes 14a and 14b and providing a long-term stable measurement. This function is disclosed in U.S. Pat. No. 3,929,587 which is hereby incorporated by reference in its entirety into this disclosure.

Electrodes 18a and 18b perform a still separate function which is integral to the operation of the sensing device 10 when measuring in the ppb range. They provide a mechanism which removes the dissolved oxygen from the electrolyte retained in the cell cavity 12. This is important because the presence of even trace amounts of dissolved oxygen will produce current and impede the accurate analysis of ppb levels of oxygen in the gaseous sample stream. The power conditioner 20 provides a potential of approximately 1.5 VDC between electrodes 18a and 18b. In this potential range, hydrogen is evolved on the electrode 18a. The details of this function are disclosed in U.S. Pat. No. 4,960,497 which is hereby incorporated by reference in its entirety into this disclosure.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described my invention, what I now claim is:

1. A method for measuring the amount of oxygen in a gas which includes:
    establishing in an electrolyte an electrolytic path between sensing electrodes comprising a cathode and a metal composite anode;
    flowing the gaseous stream in contacting relationship with the cathode;
    reducing the oxygen at the cathode to form hydroxyl ions;
    reacting electrically the hydroxyl ions at the metal composite anode to oxidize the metal anode, the metal anode characterized in that no discrete chemical reaction byproducts are formed and its potential remains stable;
    establishing a current which current is linear to the rate at which the oxygen is reduced at the cathode; and
    measuring said current.
2. The method of claim 1 which includes:
    flowing the gas into a cavity; and
    metering the gas from the cavity through a diffusion plate to the cathode.
3. The method of claim 2 which includes:
    flowing the gas into the cavity at a rate of 0.5 and 3.0 scfh.
4. The method of claim 2 where the gas is at a temperature between about 32° and 125° F.
5. The method of claim 2 where the sample is at a pressure of about 1.0 psig.
6. The method of claim 1 wherein the electrolyte is aqueous 0.1–10 M KOH.
7. The method of claim 1 wherein the cathode is a catalyzed carbon-polytetrafluoroethylene electrode specific to oxygen reduction.
8. The method of claim 1 wherein the anode is a nickel hydroxide composite and which comprises:
    oxidizing the nickel from +2 to +3, the oxidized nickel +3 remaining in situ on the anode.
9. The method of claim 8 which comprises:
    defining a period of non-measurement of the oxygen; and
    reducing the oxidized nickel on the anode during said period of non-measurement.
10. The method of claim 9 which comprises:
    reducing the oxidized nickel without the formation of discrete chemical reaction byproducts.
11. The method of claim 1 which comprises:
    applying a polarographic potential between the cathode and the anode; and
    controlling the polarization of the cathode based on the anode acting as a fixed reference potential.
12. The method of claim 1 wherein the anode is selected from the group consisting of $MnO_2/MnOOH$, $Ag_2O/Ag_2O_2$, $Hg/HgO$, $Ni(OH)_2/NiOOH$.
13. The method of claim 1 wherein the electrolytic path between the cathode and the anode is a first electrolytic path and which includes:
    providing a first barrier electrode and a second electrode, the barrier electrode interposed between the cathode and the bulk electrolyte, the first and second electrodes completing a second electrolytic path, the function of which is independent of the function of the first electrolytic path; and
    applying a voltage across the first and second electrodes to activate the barrier electrode such that unwanted components in the electrolyte are electrolytically inhibited from diffusing to the cathode.
14. The method of claim 13 which includes:
    providing a reservoir of electrolyte in communication with the electrolyte of the cell and wherein the second electrode is disposed in the reservoir, the electrolytes of the cell and the reservoir is in fluid flow communication.

15. The method of claim 13 which includes:
polarizing the first barrier electrode to evolve hydrogen on said first barrier electrode while generating oxygen at the second electrode.

16. The method of claim 15 wherein the oxygen generated at the second electrode effervesces from the reservoir.

17. The method of claim 15 where the current between the barrier electrode and the second electrode is equivalent to the equilibrium concentration of $O_2$ available at the barrier electrode.

18. The method of claims 1 or 13 wherein the electrolytic path between the cathode and the anode is a first electrolytic path and which includes:
providing a reservoir of electrolyte in communication with the electrolyte and producing a third pair of electrodes, one of said electrodes disposed in the reservoir of electrolyte and the other of said electrodes disposed in the electrolyte, which pair of electrodes provides a third electrolytic path, the function of which path is independent of the function of the first and second electrolytic paths;
generating a current between the third pair of electrodes resulting in a pH gradient between the electrolyte of the reservoir and the electrolyte to provide for the migration of unwanted ionic species from the electrolyte to the reservoir, which unwanted species do not directly affect reactions at the cathode; and
restricting the back diffusion of the unwanted ionic species from the reservoir into the cell, whereby the unwanted ionic species remain segregated from the electrolyte.

19. The method of claim 18 which includes:
establishing a zone of hydroxyl ions in the electrolyte of the reservoir of a different concentration than the hydroxyl ions in the bulk electrolyte.

20. The method of claim 18 which includes:
emitting the ionic species from the reservoir by effervescence.

21. The method of claim 18 which includes:
emitting the ionic species by direct oxidation at the anode.

22. The method of claim 18 which includes:
scavenging the ionic species via electrode surface adsorption.

23. A system for measuring the amount of oxygen in a gas which comprises:
an electrochemical cell having a metal anode and a cathode and an electrolyte;
means to apply a polarographic potential to the anode to control the cathodic potential;
means to establish an electrolytic path between the cathode and the anode;
means to meter the gas to the cathode;
means to reduce the oxygen at the cathode to form hydroxyl ions;
means to oxidize the metal anode, the anode characterized in that no discrete chemical reaction by-products are formed and to establish a current which current is linear to the rate at which the oxygen is reduced at the cathode; and
means to measure the oxygen reduced.

24. The system of claim 23 wherein the electrolyte is aqueous 0.1–10 M KOH.

25. The system of claim 23 which includes:
a cavity into which the gas flows and a diffuser plate interposed between the cavity and the cathode to meter the gas to the cathode.

26. The system of claim 23 wherein the cathode is a catalyzed carbon-polytetrafluoroethylene electrode specific to oxygen reduction.

27. The system of claim 23 wherein the anode is selected from the group consisting of $Ni(OH)_2/NiOOH$, $MnO_2/MOOH$, $Ag_2O/Ag_2O_2$, $Hg/HgO$.

28. The system of claim 27 wherein the anode is a nickel hydroxide composite.

29. The system of claim 23 which comprises:
a first barrier electrode and a second electrode, the first and second electrodes completing a second electrolytic path, the function of which is independent of the function of the first electrolytic path; and
means to apply a voltage across the first and second electrodes to activate the barrier electrode such that unwanted components in the electrolyte are electrolytically inhibited from diffusing to the cathode.

30. The system of claim 29 which comprises:
a reservoir of electrolyte in communication with the electrolyte in the cell, the second electrode disposed in the reservoir, the reservoir and the electrolyte in the electrochemical cell in fluid flow communication.

31. The system of claim 30 which includes:
means to polarize the first barrier electrode to a potential at which dissolved oxygen is instantaneously consumed, at the second electrode, oxygen is produced and released into the reservoir electrolyte.

32. The system of claims 23 or 29 which includes:
a reservoir of electrolyte in communication with the electrolyte of the electrochemical cell;
wherein the anode and the cathode are a first pair of electrodes and the first barrier electrode and its associated second electrode are a second pair of electrodes and which system has a third pair of electrodes, one of the electrodes of said third pair in the reservoir of electrolyte and the other of the electrodes disposed in the electrolyte of the electrochemical cell, the third pair of electrodes providing a third electrolytic path, the function of which path is independent of the function of the first or second electrolytic paths;
means to generate a current between the third pair of electrodes resulting in a pH gradient between the electrolyte or the reservoir and the electrolyte of the electrochemical cell, the third electrolytic path providing means for the migration of unwanted ionic species from the electrolyte to the reservoir; and
means to restrict the back diffusion of the unwanted ionic species from the reservoir into the cell.

* * * * *